United States Patent
Zhou et al.

(10) Patent No.: US 9,179,836 B2
(45) Date of Patent: Nov. 10, 2015

(54) COMPACT WAVEFRONT SENSOR MODULE AND ITS ATTACHMENT TO OR INTEGRATION WITH AN OPHTHALMIC INSTRUMENT

(71) Applicant: Clarity Medical Systems, Inc., Pleasanton, CA (US)

(72) Inventors: Yan Zhou, Pleasanton, CA (US); William Shea, Pleasanton, CA (US)

(73) Assignee: CLARITY MEDICAL SYSTEMS, INC., Pleasanton, CA (US)

( * ) Notice: Subject to any disclaimer, the term of this patent is extended or adjusted under 35 U.S.C. 154(b) by 149 days.

(21) Appl. No.: 13/964,928

(22) Filed: Aug. 12, 2013

(65) Prior Publication Data
US 2014/0022509 A1    Jan. 23, 2014

Related U.S. Application Data

(63) Continuation of application No. 13/154,293, filed on Jun. 6, 2011, now Pat. No. 8,506,083.

(51) Int. Cl.
*A61B 3/10* (2006.01)
*G01J 9/00* (2006.01)
(Continued)

(52) U.S. Cl.
CPC ............... *A61B 3/1015* (2013.01); *G01J 9/00* (2013.01); *A61B 19/5223* (2013.01); *G02B 27/0018* (2013.01)

(58) Field of Classification Search
CPC .................................................. A61B 3/1015
USPC ................... 351/221, 246, 206, 205; 359/389; 606/4, 5
See application file for complete search history.

(56) References Cited

U.S. PATENT DOCUMENTS 6,536,900 B2    3/2003    Mihashi et al.
6,561,648 B2    5/2003    Thomas
(Continued)

FOREIGN PATENT DOCUMENTS

EP    1 618 838 A1    1/2006
EP    2 103 249 A1    9/2009
(Continued)

OTHER PUBLICATIONS

Liang, J. et al., "Objective measurements of wave aberrations of the human eye with the use of a Hart-Shackman wave-front sensor", J. Opt. Soc. Am. A., vol. 11, No. 7, Jul. 1994, pp. 1949-1957, copyright 1994 Optical Society of America.
(Continued)

*Primary Examiner* — Hung Dang
(74) *Attorney, Agent, or Firm* — Kilpatrick Townsend & Stockton LLP (57) ABSTRACT

One embodiment disclosed is a compact wavefront sensor module to be attached to or integrated with an ophthalmic instrument for eye examination and/or vision correction procedures. The front lens for relaying the wavefront from the eye to a wavefront sampling plane is positioned at the optical input port of the wavefront sensor module. The front lens is shared by the wavefront sensor and the ophthalmic instrument, and the wavefront sensor module can be made very compact while still being able to cover a large eye wavefront measurement diopter range. Another embodiment disclosed is an ophthalmic device for measuring properties of a subject eye including an ophthalmic instrument integrated with the wavefront sensor module.

18 Claims, 6 Drawing Sheets

(51) Int. Cl.
*A61B 19/00* (2006.01)
*G02B 27/00* (2006.01)

(56) References Cited

U.S. PATENT DOCUMENTS

| | | |
|---|---|---|
| 6,572,230 B2 | 6/2003 | Levine |
| 6,685,319 B2 | 2/2004 | Watson |
| 7,057,806 B2 | 6/2006 | Atkinson |
| 7,445,335 B2 | 11/2008 | Su |
| 7,815,310 B2 | 10/2010 | Su |
| 7,883,505 B2 | 2/2011 | Van Heugten et al. |
| 8,100,530 B2 | 1/2012 | Zhou |
| 2005/0007551 A1 | 1/2005 | Wakil et al. |
| 2006/0203196 A1 | 9/2006 | Van Heugten |
| 2007/0252951 A1 | 11/2007 | Hammer et al. |
| 2007/0291230 A1 | 12/2007 | Yamaguchi et al. |
| 2008/0018855 A1 | 1/2008 | Larichev et al. |
| 2010/0110379 A1 | 5/2010 | Zhou |
| 2010/0208203 A1 | 8/2010 | Sarver |
| 2010/0231858 A1 | 9/2010 | Su |
| 2012/0147460 A1* | 6/2012 | Kubler et al. ............... 359/389 |

FOREIGN PATENT DOCUMENTS

| | | |
|---|---|---|
| JP | 2001-275972 | 10/2001 |
| KR | 10-2007-0004550 | 1/2007 |
| WO | 03/020167 A2 | 3/2003 |
| WO | 2005/048829 A2 | 6/2005 |

OTHER PUBLICATIONS

Widiker, J et al. "High-speed Shack-Hartmann wavefront sensor design with commercial off-the-shelf optics", Applied Optics, vol. 45, Jan. 2006, pp. 393-395, copyright 2006 Optical Society of America.

Goodman, J, "Introduction to Fourier Optics, Second Edition", The McGraw- Hill Companies, Inc.1998, pp. 232-233, 273-274, copyright The McGraw -Hill Companies, Inc. 1996, 1968.

Zawadzki, Robert J. et al., "Challenges and possibilities for developing adaptive optics—ultra-high resolution optical coherence tomography for clinical in vivo retinal imaging," Proc of SPIE, vol. 7139, Dec. 30, 2008, pp. 71390X-1 to 71390X-9.

* cited by examiner

COMPACT WAVEFRONT SENSOR MODULE AND ITS ATTACHMENT TO OR INTEGRATION WITH AN OPHTHALMIC INSTRUMENT

RELATED APPLICATIONS

This application is a continuation of U.S. application Ser. No. 13/154,293, filed Jun. 6, 2011, entitled "A COMPACT WAVEFRONT SENSOR MODULE AND ITS ATTACHMENT TO OR INTEGRATION WITH AN OPHTHALMIC INSTRUMENT," now U.S. Pat. No. 8,506,083, the entire contents of which are incorporated herein by reference for all purposes.

TECHNICAL FIELD

One or more embodiments of the present invention relate generally to ophthalmic wavefront sensors and particularly relate to wavefront sensor modules and their attachment to or integration with an ophthalmic instrument for vision correction surgical procedures.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which, in and of themselves, may also be inventions.

Wavefront sensors for ophthalmic applications are generally bulky and stand-alone desktop instruments. Although there have been attempts to integrate a wavefront sensor with an ophthalmic instrument such as a LASIK system (see for example, U.S. Pat. No. 6,685,319), a fundus camera (see for example, U.S. Pat. No. 6,572,230), and a confocal scanning laser, ophthalmoscope (see for example, U.S. Pat. No. 7,057,806), these integrated systems generally do not have important size concerns. There was, therefore, no need to make the wavefront sensor module extremely compact.

DESCRIPTION OF EXAMPLE EMBODIMENTS

OVERVIEW

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

One embodiment of the present invention is a compact wavefront sensor module to be attached to or integrated with an ophthalmic instrument such as a surgical microscope for eye examination and/or vision correction procedures, comprising: a front lens, being the first lens of a wavefront relay, disposed at the optical input port of the wavefront sensing module; a dichroic or short pass beam splitter/combiner configured to allow most of the light meant for the ophthalmic instrument to pass through and to reflect typically a near infrared wavefront beam from the eye to the wavefront relay path; and a compensating lens configured to transmit the spectrum of light meant for the ophthalmic instrument and/or to compensate the influence to the ophthalmic instrument's optical view and/or beam introduced by the front lens; wherein the front lens is shared by the wavefront sensor module and the ophthalmic instrument.

Another embodiment of the present invention is an ophthalmic device for measuring optical properties of an eye, comprising: an ophthalmic instrument with or without its original objective lens, and a compact wavefront sensor configured to be attached to or integrated with the ophthalmic instrument, wherein the wavefront sensor comprises a front lens, being the first lens of a wavefront relay, disposed at the optical input port of the wavefront sensing module; and a beam splitter configured to allow most of the light meant for the ophthalmic instrument to pass through and to reflect typically a near infrared wavefront beam from the eye to the wavefront relay path; wherein the front lens is shared by the wavefront sensor module and the ophthalmic instrument.

One object of the present invention is to make the wavefront sensor module more compact than existing designs. Another object of the present invention is to cover a large wavefront diopter measurement range needed for an ophthalmic procedure such as a cataract refractive vision correction procedure. Both objectives are achieved in an example embodiment by arranging the first relay lens of the wavefront sensor as close to the patient's eye as physically feasible while still allowing the surgeon to perform the ophthalmic procedure such as vision correction and/or refractive surgical operation as is normally done without any change in ergonomics.

Other features and advantages of the present invention will become more readily apparent to those skilled in the art upon review of the following detailed description of the preferred embodiments taken in conjunction with the accompanying drawings.

Description

In accordance with one or more example embodiments, the first lens for relaying the wavefront from a patient's eye to a wavefront sampling plane is disposed as a shared front lens at the optical input port of the wavefront sensor module or the ophthalmic instrument. This configuration allows the overall optical path length for relaying the wavefront from the eye to a wavefront sampling plane to be relatively short and the wavefront beam width variation range for covering a desired wavefront diopter measurement range to also be relatively small. Consequently, the physical size or form factor of the wavefront sensor module can be made very compact while a desired wavefront measurement diopter range can still be covered.

In recent years it has been realized that there is a need for a real time wavefront sensor to provide live feedback for various vision correction procedures such as LRI/AK refinement, Laser Enhancement, and cataract and refractive surgery. A simple way to integrate a wavefront sensor to an existing ophthalmic instrument such as a surgical microscope is to attach or integrate a wavefront sensor module next to the objective lens of the ophthalmic instrument or to incorporate the wavefront sensor inside the ophthalmic instrument. Generally, in order to minimize the influence of the wavefront sensor module to the viewing optical path of the ophthalmic instrument, and to minimize attachment/integration complexity, such a wavefront sensor module is designed with no lens shared between the wavefront sensor and the ophthalmic instrument (see for example, U.S. Pat. No. 7,883,505).

However, such a wavefront sensor module can suffer from a limited diopter measurement range, and/or loss of optical energy or lower signal-to-noise performance. Additionally, if the physical size of the wavefront sensor module is too large it can interfere with the normal operation technique of a vision correction surgeon.

In light of the above, there is a need in the art for a compact wavefront sensor module that, when attached to or integrated with an ophthalmic instrument such as a surgical microscope, will not interfere with a surgeon's normal vision correction operation technique or ergonomics, and meanwhile will provide a diopter measurement range large enough to cover the need required for the vision correction procedures that can occur at the point of surgery or eye examination.

Figure 1:
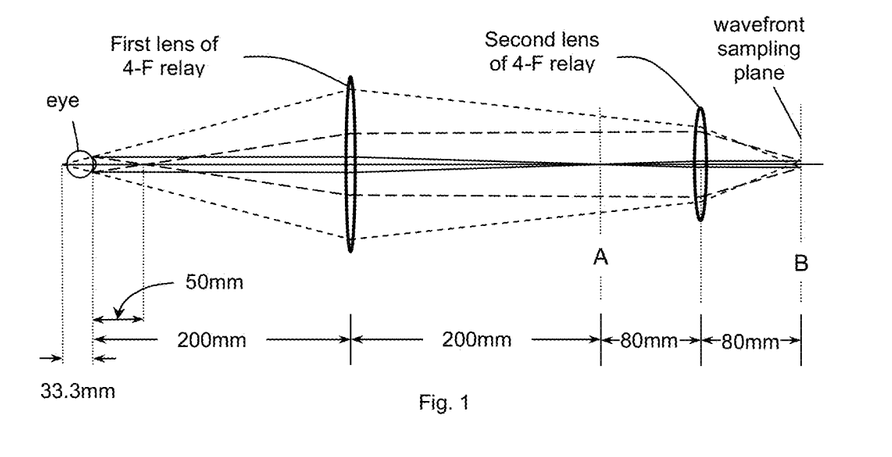
FIG. 1 shows a typical 4-F optical wavefront relay configuration.

In order to appreciate the advantages of arranging the first wavefront relay lens as close as physically practical to the patient eye, let us first take a look at an example 4-F optical wavefront relay configuration as shown in FIG. 1 with the wavefront beam path unfolded for an easy explanation.

In a typical wavefront sensor used for the measurement of wavefront aberration of a human eye, the wavefront from the subject eye pupil or cornea plane is generally relayed to a wavefront sensing or sampling plane using the well known 4-F relay principle once, twice or multiple times (see for example, J. Liang, et al. (1994) "Objective measurement of the wave aberrations of the human eye with the use of a Hartmann-Shack wave-front sensor," J. Opt. Soc. Am. A 11, 1949-1957; J. J. Widiker, et al. (2006) "High-speed Shack-Hartmann wavefront sensor design with commercial off-the-shelf optics," Applied Optics, 45(2), 383-395; U.S. Pat. No. 7,654,672). Such a 4-F relay system will preserve the phase information of the incident wavefront while allowing it to be relayed without detrimental propagation effects. In addition, by configuring an afocal imaging system using two lenses of different focal lengths to realize the 4-F relay, the relay can allow for the magnification or demagnification of the incident wavefront with an associated demagnification or magnification of the divergence or convergence of the incident wavefront (see for example, J. W. Goodman, Introduction to Fourier Optics, 2nd ed. McGraw-Hill, 1996).

In the example of FIG. 1, the first lens of the 4-F relay has a diameter of 40 mm and an effective focal length of 200 mm, which is the typical focal length (or the working distance) of a standard ophthalmic surgical microscope. The eye is located at or near the front focal plane of the first lens of the 4-F wavefront relay. The Fourier transform plane A of the 4-F wavefront relay is at the back focal plane of the first lens and the front focal plane of the second lens of the 4-F wavefront relay as shown by the vertical dashed line represented by the capital letter A. In this example, the second lens of the 4-F wavefront relay has a diameter of 30 mm and an effective focal length of 80 mm. The relayed wavefront image plane of the 4-F wavefront relay is at the back focal plane of the second lens as shown by the vertical dashed line represented by the capital letter B. Due to the difference in the effective focal length of the two lenses used in the 4-F wavefront relay configuration, the replica or image of the incident wavefront from the eye is optically de-magnified in the transverse dimension by 200/80=2.5 times, as is well known to those skilled in the art.

As can be seen from FIG. 1, when the eye is emmetropic and hence the wavefront from the eye is close to being planar, the light beam from the eye is a relatively narrow and parallel beam as represented by the solid light rays. If the eye pupil has a diameter of 5 mm, for example, the beam will be about 5 mm in diameter. The exact beam shape is also dependent on the light scattering spot size on the retina which is a function of a light beam (typically a superluminescent diode (SLD) beam which is not shown in FIG. 1) being delivered to the eye to create the wavefront. After passing through the first lens of the 4-F wavefront relay, the wavefront beam from the eye will be focused on the optical axis at the first Fourier transform plane A where it will transform from a convergent beam to a divergent beam. The beam is re-collimated by the second lens of the 4-F wavefront relay, and the beam diameter will be reduced to 2 mm because of the difference in the effective focal length of the two lenses used in the 4-F wavefront relay.

If the eye is aphakic or highly hyperopic or highly myopic, the wavefront from the eye will no longer be planar but very divergent or convergent. In other words, the beam from the eye will no longer be a relatively parallel beam; instead, it will be either a highly divergent or a highly convergent conical beam. For typical cataract refractive surgery applications, the desired diopter range that should be covered by an intraoperative wavefront sensor should be from a hyperopic +30 D to a myopic −20 D (we define a divergent wavefront from an eye as having positive diopter value and a convergent wavefront from an eye as having negative diopter value).

The shorter dashed light rays in FIG. 1 shows the case of a divergent wavefront with a diopter value of +30 D, which represents normal aphakia (with a typical hyperopic diopter value of +20 D) plus an additional cornea induced hyperopia of +10 D. As can be seen, when the divergent conical beam from the eye, as represented by the shorter dashed light rays, propagates to the first lens, it will be intercepted by the first lens and changed from a highly divergent beam to a slightly convergent beam. In fact, if the eye pupil is 5 mm in diameter and the wavefront from the eye has a hyperopic diopter value of +30 D, this is equivalent to a divergent beam in free space coming from a point source located at 33.3 mm behind the eye pupil plane or 233.3 mm away from the first lens of the 4-F wavefront relay. This highly divergent conical beam is limited by the 5 mm eye pupil at 33.3 mm from the point source location to form a highly divergent conical beam that, when reaching the first lens location of the 4-F wavefront relay, will be 35 mm in diameter. When the beam reaches the Fourier transform plane A, the beam width will be 30 mm in diameter. When the beam reaches the second lens, the beam width will be 28 mm.

The longer dashed light rays in FIG. 1 show a highly myopic wavefront beam of −20 D, i.e. a highly convergent conical beam from the eye that will converge to a point after leaving the eye at a distance of 50 mm and transform to a highly divergent conical beam as represented by the longer dashed light rays. As this −20 D wavefront beam is narrower than the +30 D beam in most of the wavefront relay beam path except near the end of the wavefront sampling plane, it is the +30 D beam that determines the diameter of the lens required to intercept the entire cone of light.

It should be noted that in addition to spherical refractive error or defocus, other optical aberrations of the eye such as astigmatism, coma and trefoil will cause the beam coming out from the eye to no longer be conic, but the maximum beam width will still be determined by the eye pupil size and the extreme or cumulative diopter value(s) on a certain meridian plane.

From the above discussion, it can be seen that given the eye pupil size and the diopter range to be covered, the beam cone angle variation range can be determined. To achieve high resolution measurements it is desirable to capture all the wavefront light returned from the eye with the first lens. Accordingly, depending on how far the first lens is from the eye, this beam cone angle variation range will determine the diameter of the first lens. In addition, the distance from the eye to the first lens will also determine the focal length of the first lens per the requirement of a 4-F wavefront relay and therefore, will, in turn, affect the overall optical path length of the 4-F wavefront relay.

Figure 2:
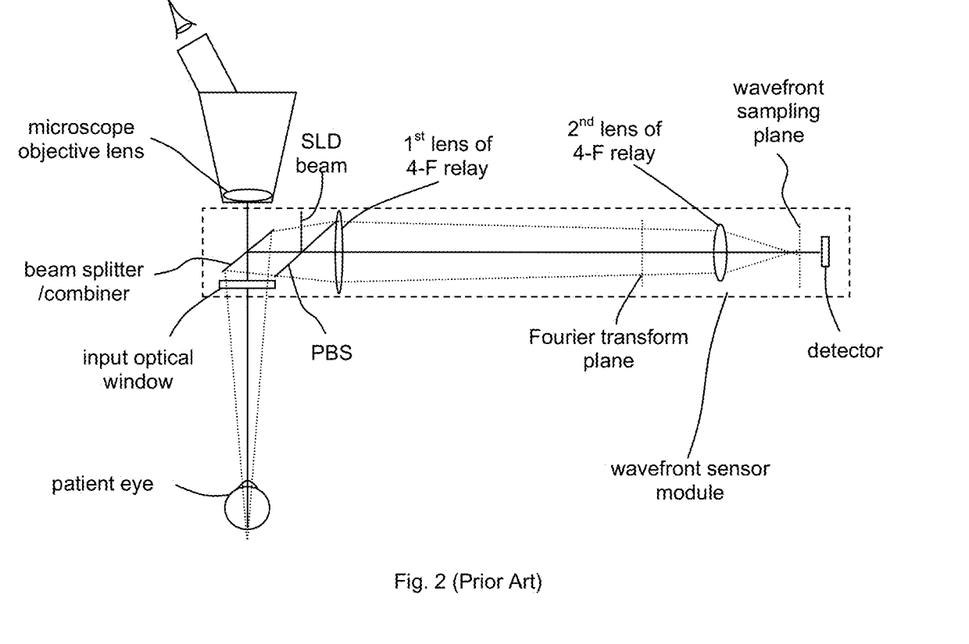
FIG. 2 shows a prior art optical configuration of a wavefront sensor module when attached to a surgical microscope below the objective window of the microscope.

FIG. 2 shows an example of an optical configuration of a wavefront sensor module attached to a surgical microscope (see for example, U.S. Pat. No. 7,883,505). A visual light source associated with the surgical microscope emits visual light that illuminates the patient eye and a microscope viewing beam is returned from the patient eye to the objective of the surgical microscope. An SLD beam also illuminates the patient eye with near infrared (NIR) light and a wavefront sensing beam is returned from the patient eye to a detector of the wavefront sensor.

In this configuration, the first lens for relaying the wavefront beam is arranged after an input optical window and a beam splitter/combiner that transmits the microscope viewing beam and deflects the wavefront sensing beam sideways, and a polarization beam splitter (PBS) used for reflecting a s-polarized superluminescent diode (SLD) beam to the eye and transmitting a p-polarized wavefront beam from the eye to the rest of the wavefront sensor. The first lens of the 4-F relay is oriented vertically inside of the wavefront sensor housing. The orientation of the first lens requires that the height (thickness) of the wavefront sensor housing be greater than the diameter of the first lens.

If the working distance of the ophthalmic surgical microscope is the same as the focal length of the objective lens of the microscope and is about 200 mm as we have discussed in FIG. 1, then the first lens will be about 250 mm away from the eye (the distance from the eye to the beam splitter/combiner added to the distance from the beam splitter/combiner to the first lens) considering also the existence of the PBS. Assuming that the same ratio of 2.5 is maintained between the first lens focal length and the second lens focal length of the 4-F wavefront relay, the second lens needs to have a focal length of 100 mm. Consequently, the total wavefront relay path length will be (250×2+100×2)=700 mm.

In addition, when a +30 D hyperopic wavefront beam from a 5 mm eye pupil reaches the first lens, its beam width will be 42.5 mm due to the increased distance from the eye (250 mm instead of 200 mm) and therefore a lens having a diameter of at least 42.5 mm is required to intercept the entire cone of light emitted by the eye. Given the fact that the first lens is positioned vertically, which means that extra vertical space is needed for mounting this lens, and that a 50 mm diameter lens will most likely have to be used per the consideration of an 85% clear aperture and the commercial availability of off-the-shelf lenses, the height of the wavefront sensor module at the vertical first wavefront relay lens location will most likely be greater than 50 mm.

This optical configuration has no shared lens between the wavefront beam path and the microscope viewing beam path and thus has the advantage that the microscope viewing optical beam is minimally affected by the wavefront sensor module. In addition, by arranging the first lens of the 4-F wavefront relay after the PBS for directing the SLD beam to the eye, the SLD beam is also not affected by the first lens. However, these advantages are achieved at the expense of increased physical size of the wavefront sensor module. Further, if a first lens of smaller diameter is used to decrease the height/thickness of the wavefront sensor module then the diopter measurement range or signal to noise ratio will be reduced.

Owing to the fact that most cataract surgeons prefer and are accustomed and trained to the larger working space between the surgical microscope's objective lens and the patient's eye, it is thus desirable to keep the height of the wavefront sensor module as small as possible while still being able to cover a large enough wavefront measurement diopter range and not alter or interfere with the surgeon's or their staff's ergonomics.

Figure 3:
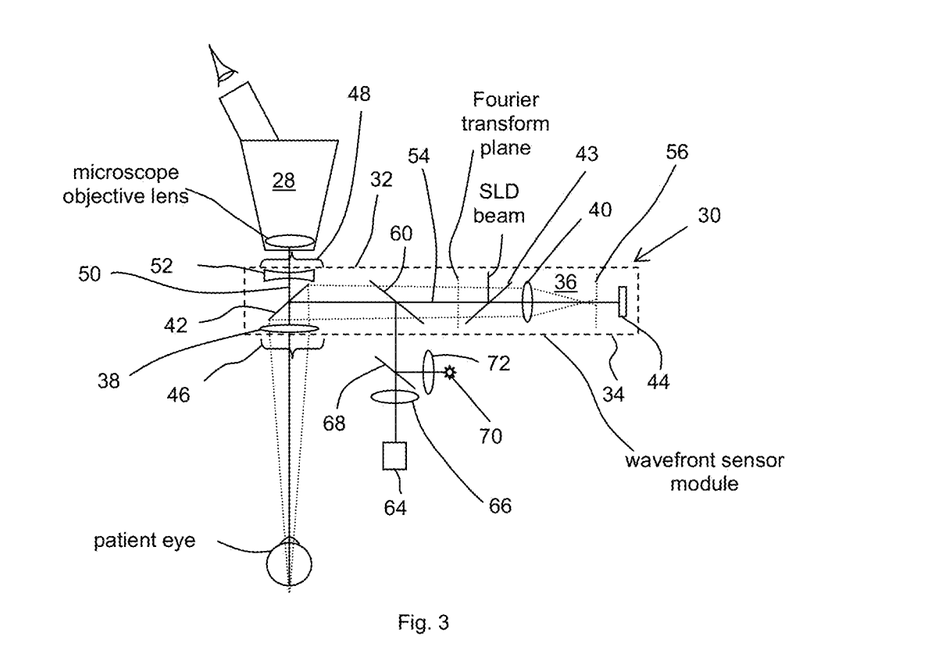
FIG. 3 shows a schematic diagram of an example embodiment of the present invention, in which the first lens of the 4-F wavefront relay is disposed as a front lens at the optical input port of the wavefront sensor module and is shared with a microscope.

FIG. 3 shows a schematic diagram of one example embodiment of a wavefront sensor module that is compact and also has large dynamic range with minimal loss of wavefront beam optical energy from the eye.

In FIG. 3, the wavefront sensor module includes a housing 30 having upper and lower surfaces 32 and 34 and an interior 36 in which are disposed first and second lenses 38 and 40 of a 4-F relay, a dichroic or short pass beam splitter 42, a polarizing beam splitter 43 and a detector 44. The housing 30 includes a first optical window 46 in the lower surface 34 and a second optical window 48 in the upper surface 32. The first and second optical windows are aligned so that a first optical path 50 is formed between the first and second windows 46 and 48 that allows light returned from the patient eye to pass through the housing 30 to the objective lens of the surgical microscope. A compensating lens 52 is located at the second optical window 48 and the dichroic or short pass beam splitter 42 is positioned in the first optical path 50.

In the example embodiment depicted in FIG. 3, the dichroic or short pass beam splitter 42 reflects a near infrared wavefront beam as well as some imaging light along a second optical path 54. The 4-F relay relays the wavefront from the subject eye to the wavefront sampling plane 56. The detector 44 (together with some other optical elements such as a lenslet or a lenslet array or a grating, which are not shown) samples and detects the wavefront relayed to the wavefront sampling plane 56.

In this example embodiment, an imaging beam splitter 60 is also inserted into the second optical path 54. The imaging beam splitter 60 directs at least some of the imaging light reflected from the dichroic or short pass beam splitter 42 to an image sensor 64, such as a CCD/CMOS camera, via a lens or set of lenses 66. The image sensor 64 provides a coplanar video or static image of a subject eye. Further, a fixation beam splitter 68 directs the image of a fixation target 70, formed by a lens or set of lenses 72, along a reverse path to the subject eye.

In this example embodiment, the microscope objective lens is kept as it would be in the microscope housing and the first lens of the 4-F wavefront relay is positioned at the very first optical input port of the wavefront sensor module. The first lens is shared by the surgical microscope and the wavefront sensor module.

Among the benefits of arranging this first lens of the 4-F wavefront relay as close as possible to the patent's eye is that: (1) the first (front) lens of the 4-F wavefront relay has the shortest focal length that meets the requirements of a 4-F wavefront relay, and (2) the overall length of the wavefront beam path inside the wavefront module is shortened.

In addition, for a certain eye diopter measurement range to be covered per a certain eye pupil size, the diameter range of the wavefront beam cone when reaching this front lens is reduced because the first (front) lenses of the 4-F relay is closer to the eye and therefore the height of the wavefront module can be reduced. These physical dimension reductions combined with further folding of the wavefront beam path can make the wavefront sensor module very compact. Furthermore, since there is always a need for the wavefront sensor module to have an optical window at this location, in some example embodiments the front shared lens can serve the dual purpose of being both the window and the first lens of the 4-F wavefront relay.

We can now do an approximate comparison of the physical dimensions of the wavefront sensor module depicted in FIG. 3 and the prior art wavefront sensor module depicted in FIG. 2. In the embodiment depicted in FIG. 3, if the working distance of the ophthalmic surgical microscope is still the same as the focal length of the objective lens of the microscope and is about 200 mm as we have discussed in FIG. 1, then the first lens can now be about 170 mm away from eye. We will again assume that the same ratio of 2.5 is to be maintained between the first lens focal length and the second lens focal length. Since the first lens now has a focal length of only 170 mm instead of 250 mm as in FIG. 2, the second lens now needs to have a focal length of 68 mm instead of 100 mm as in FIG. 2. Therefore, the total wavefront relay path length will now be (170×2+68×2)=476 mm instead of the 700 mm of the example depicted in FIG. 2, which is a reduction in physical length of the 4-F wavefront relay depicted in FIG. 3 over the example depicted in FIG. 2 by (700−476)/700=32%.

In terms of the height of the wavefront sensor module, with the same +30 D hyperopic beam from a 5 mm eye pupil reaching the first lens, the beam width at the first lens in the FIG. 3 embodiment will be 30 mm instead of the 42.5 mm of the FIG. 2 example. This implies that after the highly divergent wavefront beam is focused by the shared front lens to be slightly convergent and is deflected sideways, its diameter will be less than 30 mm. Note that since the first lens is lying horizontally in the FIG. 3 embodiment, its diameter will not affect the height of the wavefront sensor module. Even by assuming that the shared front lens and the compensating lens will have some thickness, this thickness will not be substantially different from the configuration of the FIG. 2 example. If we assume a 5 mm additional increase in the thickness of the shared lens and the top compensating lens compared to the input optical window of FIG. 2, the FIG. 3 wavefront sensor module height will be about 35 mm instead of 50 mm as would be the case in FIG. 2. Therefore, the likely saving in terms of the height of the wavefront sensor module will be about (50−35)/50=30%.

As in the example of FIG. 2, the dichroic or short pass beam splitter/combiner as shown in FIG. 3 is used to deflect with high efficiency the SLD induced near infrared wavefront beam to the rest of the wavefront sensor module while allowing most of the visible light to pass through to the surgical microscope. It should be noted that the rest of the wavefront sensor module as shown in FIG. 3 is only one representation of a variety of potential optical configurations that can possibly be used. So the interpretation of the wavefront sensor module should cover all possible wavefront sensor configurations, including Hartmann-Shack, Talbot-Moiré, Hartmann-Moiré, Phase-diversity and laser ray tracing, for example. As such, the detector should also be interpreted in a broad sense to include all possible wavefront sampling and detection means as long as the detector effectively detects the wavefront tilt(s) at the relayed wavefront image plane. As an example, the detector can be a single lateral effect detector, a quadrant detector, or a CCD/CMOS sensor/camera arranged behind a variable aperture as disclosed in U.S. Pat. No. 7,445,335 and U.S. Pat. No. 7,815,310.

The compensating lens above the dichroic or short pass beam splitter/combiner is used to fulfill several functions. Firstly, to ensure that the surgical view to be formed and presented to the surgeon by the surgical microscope is minimally affected because of the use of the shared front lens, this compensating lens can be designed to compensate the effect of the shared front lens (the first lens of the 4-F wavefront relay) so that a substantially equivalent surgical microscopic view is presented to the surgeon. Secondly, the compensating lens can also serve as the upper optical window for physically sealing the wavefront sensor module. Further, the compensating lens can also be optically coated or treated to allow only the visible spectrum of light to be transmitted. In this manner, the near infrared and UV spectral portion of the illumination light from the microscope will not land on the patient's eye to create any eye returned near infrared background light noise that can enter the wavefront sensor module to either saturate or reduce the dynamic range of the wavefront sensor detector or to create background noise. In addition, the compensating lens also reduces the exposure to potential harmful spectral components of both the surgeon and patient. Furthermore, the compensating lens or optical window can also serve the function to direct the illumination light from inside the surgical microscope to the subject eye if the illumination beam path is affected by the shared front lens.

Figure 4:
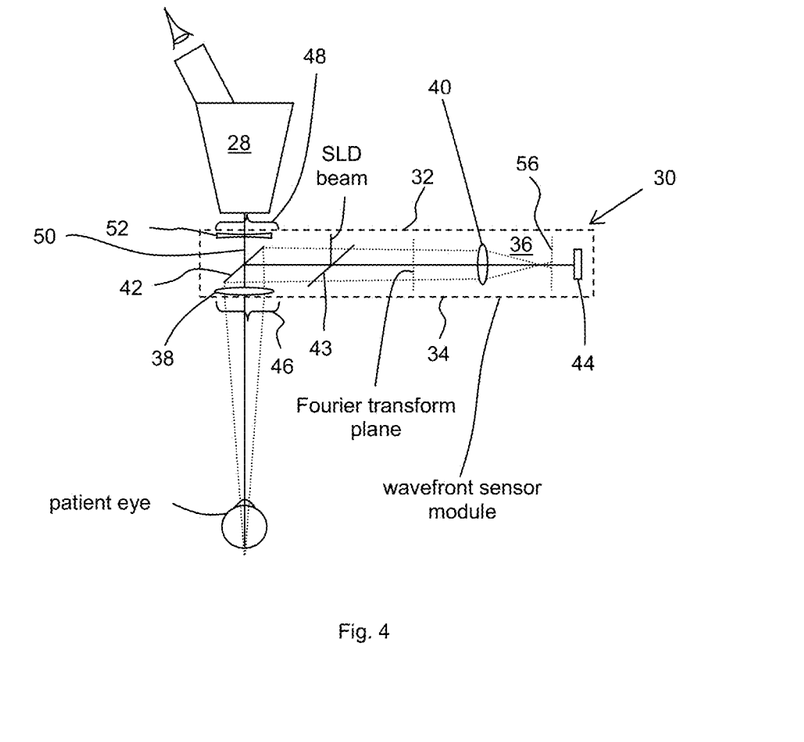
FIG. 4 shows an alternative example embodiment of the present invention, in which the objective lens of the microscope is removed and its focusing function is either fully or partially served by the shared front lens disposed at the input port of the wavefront sensor module.

It should be noted that in the example embodiment shown in FIG. 3, the original objective lens of the surgical microscope is maintained in the microscope housing and not removed. As an alternative, the objective lens of the surgical microscope can be removed and its focusing function can be either fully or partially served by the shared front lens at the input port of the wavefront sensor module as shown in FIG. 4. The compensating lens 52 as shown in FIG. 4 can be designed to provide the desired compensation to present to the surgeon substantially the same microscopic surgical view, as well as to serve other functions as discussed above. More specifically, the compensating lens can be an optical window with only a portion of the window having light bending properties so that the illumination light from the ophthalmic instrument can be re-directed to the subject eye if the illumination beam path is changed as a result of removing the original objective lens of the microscope and arranging a shared front lens at the input port of the wavefront sensor module.

Figure 5:
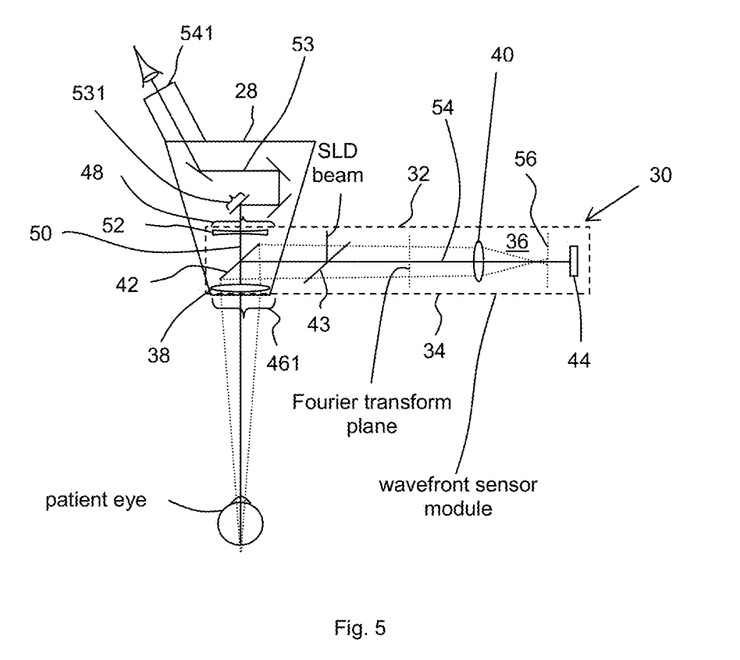
FIG. 5 shows another alternative example embodiment of the present invention, in which the wavefront sensor module is incorporated into a microscope body and the microscope's viewing path is modified.

In addition to attaching the wavefront sensor module beneath a microscope, the same concept of using a compensating lens to compensate the effect to the viewing path of a microscope as a result of sharing a lens can also be extended to the case in which a wavefront sensor is incorporated in the microscope, although there may be a need to modify or change the microscope's viewing path accordingly. FIG. 5 shows such an alternative example embodiment of a modified surgical microscope in which the original objective lens of the microscope is maintained as is and used as the shared front lens.

Refractive surgery is very precise and refractive surgeons spend years developing the hand-eye coordination required to perform microscopic eye surgery. During this development process the hand position of the surgeon relative to the surgeon's eye is typically fixed or maintained to within a preferred range. An important aspect of the design of a surgical microscope is to not require that the surgeon change hand position in order to accommodate the physical dimensions of the microscope.

In a typical stereoscopic surgical microscope, after the objective lens 38, there are two stereoscopic viewing ports/paths with their associated optical elements. In a standard stereoscopic surgical microscope these viewing ports are located close to and behind the objective lens. In the example embodiment depicted in FIG. 5 an existing design of a standard surgical microscope is modified to incorporate the surgical microscope and the wavefront sensor within a single housing. As described below, the example embodiment of FIG. 5 allows the previously designed optical components of the surgical microscope, such as the objective lens and the stereo viewing ports and their associated optical elements, to be maintained so that these components do not have to be redesigned when the wavefront sensor is integrated with the stereoscopic surgical microscope.

In the example embodiment of FIG. 5 a wavefront sensor is integrated into the housing of the stereoscopic surgical microscope and the height of the stereoscopic surgical microscope is not increased so the hand location of the surgeon is not affected by the inclusion of the wavefront sensor. Since the height of the stereoscopic surgical microscope is not increased, the working distance, e.g. 200 mm, is not affected and the original objective lens of the stereoscopic surgical microscope is used as the front lens of the 4-F relay. Since, in this example, the focal length of the first lens in the 4-F relay is 200 mm the 4-F relay is configured as depicted in FIG. 1.

In FIG. 5, the wavefront sensor includes first and second lenses 38 and 40 of a 4-F relay, a dichroic or short pass beam splitter 42, a polarizing beam splitter 43 and a detector 44. The housing of the stereoscopic surgical microscope includes an input optical window 461 and the objective lens, which also functions as the first lens 38 of the 4-F relay, is positioned at the input window 461. A compensating lens 52 is positioned so that compensating lens 52, the dichroic or short pass beam splitter 42 and first lens 38 are aligned to form a first optical path 50 between them. A folded optical path 53 extends from the pair of stereoscopic viewing ports 531, which have been offset from a position behind the objective lens to a position behind the compensating lens, to a pair of stereoscopic eyepieces 541. The folded optical path 53 includes the optical elements included in the original optical path of the standard non-modified stereoscopic surgical microscope and is of the same optical length so that the original optical elements can be maintained.

In the example embodiment depicted in FIG. 5, the dichroic or short pass beam splitter 42 reflects a wavefront beam along a second optical path 54. The 4-F relay relays the eye wavefront to the wavefront sampling plane 56. The detector 44 (together with some other optical elements such as a lenslet or a lenslet array or a grating, which are not shown) samples and detects the wavefront relayed to the wavefront sampling plane 56 to enable wavefront measurements.

In the example embodiment depicted in FIG. 5, the stereo viewing ports have been offset from the objective lens by a distance about the length of the first optical path 50. The compensating lens 52 functions to compensate the effect caused by this offset so that the microscopic view presented to the surgeon is substantially the same as if the stereoscopic viewing ports were in their original position behind the objective lens. The use of the compensating lens 52 and the folded path 53 allow the previously designed components of the stereoscopic surgical microscope to be maintained.

Alternatively, the surgical microscope with an integrated wavefront sensor can be a new design with the compensating lens and other optical components forming the folded optical path not being based on an existing design.

Figure 6:
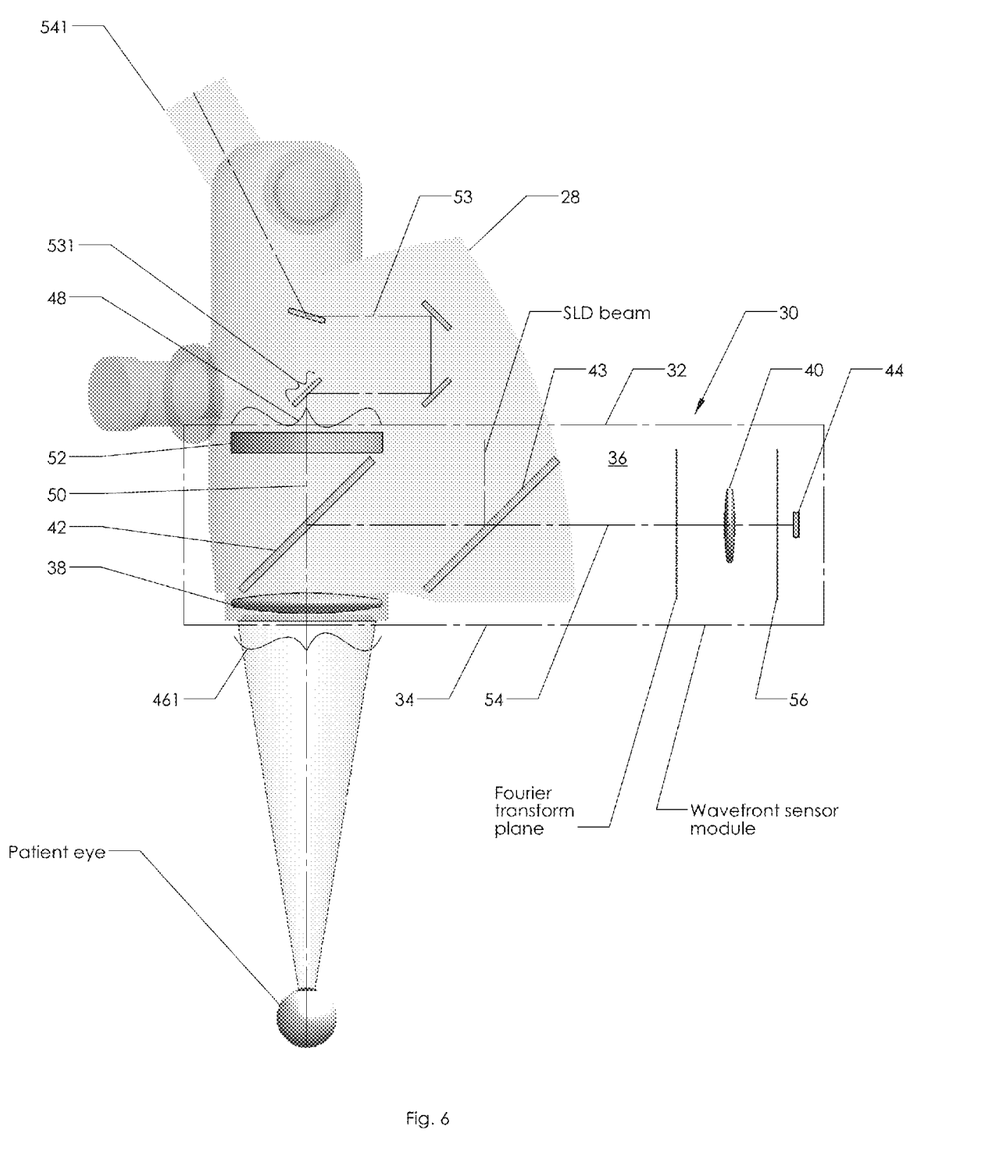
FIG. 6 is a solid works drawing depicting the example embodiment of FIG. 5.

FIG. 5 is a schematic diagram, not drawn to scale, serving to illustrate the operation of the example embodiment. FIG. 6 is a solid works drawings depicting a more realistic view of an example embodiment of an integrated surgical microscope/wavefront sensor utilizing the features described above with reference to FIG. 5.

At this point it should be noted that for the embodiments of FIGS. 3, 4 and 5, since the front lens is shared, it generally needs to pass both the visible and the near infrared spectrum of light. Preferably, it does not introduce additional optical aberrations to the wavefront beam. A good choice for this lens is an achromatic lens that is designed to work over the visible and near infrared light spectrum. As an alternative, an aspherized achromatic lens for the desired wavelength range can also be used.

Given the fact that a narrow band pass filter can be used in front of the second lens of the 4-F wavefront relay to filter out any unwanted light outside the SLD spectrum, the second lens can be designed for functioning only over the SLD near infrared spectrum range and it can also be an aspheric lens.

It should also be noted that since the front shared lens lies horizontally within the wavefront sensor module or the microscope housing, there is no absolute need to use a small diameter for this shared front lens. Its diameter can be larger so that only the central portion of the lens is used for the viewing beam path and the wavefront beam path while the outer portion can be used for properly directing the illumination beam from inside the ophthalmic microscope to the subject's eye. In addition, the PBS for directing the SLD beam to the eye can be arranged anywhere after the dichroic or short pass beam splitter/combiner, although there may be a need to shape the SLD beam accordingly. The SLD does not have to operate in the near infrared range and accordingly the beam splitter/combiner does not need be short pass or dichroic, alternatively it can be a notch filter type beam splitter/combiner or another type.

It should also be noted that the 4-F wavefront relay is only an example of various possible optical wavefront relay configurations. Other configurations can be used, such as the one disclosed in US 20100208203 that comprise three lenses with a negative lens positioned in between two positive lenses. Furthermore, various means can be employed between the relayed wavefront sampling plane and the detector for detecting the sampled wavefront tilts or other properties such as intensity. Examples include the use of a lenslet, a lenslet array, a grating, an imaging relay, etc. The detector can be any type, including one or two dimensional detector arrays such as CCD/CMOS image sensors, lateral effect position sensing detectors, quad-detectors, etc.

The presently disclosed example embodiments of the wavefront sensor module can be attached to or integrated with or incorporated into a variety of other ophthalmic microscopes for a wide range of applications. For example, the wavefront sensor module can be attached to a slit lamp biomicroscope for measuring the eye wavefront in addition to a slit lamp based eye examination. It can also be integrated with other microscopes for vision corrections such as that of a LASIK system for eye surgery.

Although various embodiments that incorporate the teachings of the present invention have been shown and described in detail herein, those skilled in the art can readily devise many other varied embodiments that still incorporate these teachings. Accordingly, it is not intended to limit the invention except as provided by the appended claims.

What is claimed is:

1. An ophthalmic device for measuring optical properties of an eye, comprising:
   an ophthalmic instrument with or without its original objective lens, and a compact wavefront sensor configured to be attached to or integrated with the ophthalmic instrument, wherein the wavefront sensor comprises:
   a front lens, being the first lens of a 4-F wavefront relay, disposed at the optical input port of the wavefront sensing module; and
   a beam splitter configured to allow most of the light meant for the ophthalmic instrument to pass through and to reflect typically a near infrared wavefront beam from the eye to the wavefront relay path;
   wherein the front lens is shared by the wavefront sensor module and the ophthalmic instrument.

2. The wavefront sensor module of claim 1, further comprising a detector disposed in the interior of the housing to detect a wavefront tilt at a wavefront image plane of the 4-F wavefront relay.

3. A wavefront sensor module comprising:
   a housing configured to be attached to or integrated with an ophthalmic instrument for eye examination and/or vision correction procedures, the housing having first and second surfaces and an interior, the first surface having a first optical window configured to pass light between the interior of the housing of the wavefront sensor module and a subject eye and the second surface having a second optical window configured to pass light between the interior of the housing and the ophthalmic instrument, wherein a first optical path is formed between the first and second optical windows to pass light between the subject eye and the ophthalmic instrument via the interior of the housing;
   a front lens, being a first lens of a 4-F wavefront relay, disposed at the first optical window of the first surface of the housing, with the front lens configured to focus light returned from the subject eye and to transmit the light along the first optical path;
   a beam splitter/combiner disposed within the housing and along the first optical path to intercept light transmitted by the front lens, with the beam splitter/combiner configured to transmit at least a portion of the light returned from the subject eye meant for the ophthalmic instrument, and to reflect at least a wavefront beam returned from the subject eye along a second optical path to the interior of the housing.

4. The wavefront sensor module of claim 3, further comprising a physical optical window element disposed at the second optical window of the second surface of the housing to seal the housing.

5. The wavefront sensor module of claim 4, wherein the physical optical window element allows only the visible spectrum of light to be transmitted.

6. The wavefront sensor module of claim 3, further comprising a second lens, being the second lens of the 4-F wavefront relay, disposed in the interior of the housing and along the second optical path.

7. An ophthalmic instrument attached or integrated with the wavefront sensor module of claim 3.

8. The ophthalmic instrument of claim 7, wherein the ophthalmic instrument comprises a surgical microscope.

9. The ophthalmic instrument of claim 7, wherein the ophthalmic instrument comprises a slit lamp bio-microscope.

10. The ophthalmic instrument of claim 7, wherein an original objective lens of the ophthalmic instrument is removed and wherein at least the front lens of the wavefront sensor module operates as an objective for the ophthalmic instrument.

11. A modified ophthalmic instrument comprising:
    a housing having an optical input port and a pair of stereoscopic eyepieces;
    an objective lens disposed at the optical input port of the housing, with the objective lens configured to function as both the first lens of a 4-F wavefront relay and the objective lens of the ophthalmic instrument to focus light returned from a subject eye and to transmit the light along a first optical path;
    a beam splitter/combiner disposed along the first optical path next to the objective lens to intercept light transmitted by the objective lens, with the beam splitter/combiner configured to transmit at least a portion of the light returned from the subject eye meant for viewing through the ophthalmic instrument, and to reflect at least a wavefront beam returned from the subject eye along a wavefront relay optical path;
    a pair of stereoscopic viewing ports disposed to receive light transmitted along the first optical path; and
    a folded optical viewing path including optical components between the pair of stereoscopic viewing ports and the pair of stereoscopic eyepieces.

12. The modified ophthalmic instrument of claim 11, further comprising an optical window element disposed along the first optical path between the pair of stereoscopic viewing ports and the beam splitter/combiner.

13. The modified ophthalmic instrument of claim 12, wherein the optical window element allows only the visible spectrum of light to be transmitted.

14. A method of modifying a surgical microscope, the method comprising:
    removing an original objective lens of the surgical microscope;
    attaching or integrating a wavefront sensor module to the surgical microscope;
    wherein the wavefront sensor module comprises:
    a housing configured to be attached to or integrated with an ophthalmic instrument for eye examination and/or vision correction procedures, the housing having first and second surfaces and an interior, the first surface having a first optical window configured to pass light between the interior of the housing of the wavefront sensor module and a subject eye and the second surface having a second optical window configured to pass light between the interior of the housing and the ophthalmic instrument, wherein a first optical path is formed between the first and second optical windows to pass light between the subject eye and the ophthalmic instrument via the interior of the housing;

a front lens, being a first lens of a 4-F wavefront relay, disposed at the first optical window of the first surface of the housing, with the front lens configured to focus light returned from the subject eye and to transmit the light along the first optical path;

a beam splitter/combiner disposed within the housing and along the first optical path to intercept light transmitted by the front lens, with the beam splitter/combiner configured to transmit at least a portion of the light returned from the subject eye meant for the ophthalmic instrument, and to reflect at least a wavefront beam returned from the subject eye along a second optical path to the interior of the housing.

15. The method of claim 14, wherein the wavefront sensor module further comprises an optical window element disposed at the second optical window of the second surface of the housing to seal the housing.

16. The method of claim 15, wherein the optical window element of the wavefront sensor module allows only the visible spectrum of light to be transmitted.

17. A wavefront sensor module comprising:
a housing configured to be attached to or integrated with an ophthalmic instrument for eye examination and/or vision correction procedures when an objective lens, normally included in the ophthalmic instrument has been removed, the housing having first and second surfaces and an interior, the first surface having a first optical window configured to pass light between the interior of the housing of the wavefront sensor module and a subject eye and the second surface having a second optical window configured to pass light between the interior of the housing and the ophthalmic instrument, wherein a first optical path is formed between the first and second optical windows to pass light between the subject eye and the ophthalmic instrument via the interior of the housing;

a front lens, being a first lens of a 4-F wavefront relay, disposed substantially at the first optical window of the first surface of the housing, with the front lens configured to fully or partially perform the focusing function of a removed objective lens on light returned from the subject eye and to transmit the light along the first optical path;

a beam splitter/combiner disposed within the housing and along the first optical path to intercept light transmitted by the front lens, with the beam splitter/combiner configured to transmit at least a portion of the light returned from the subject eye meant for the ophthalmic instrument, and to reflect at least a wavefront beam returned from the subject eye along a second optical path to the interior of the housing.

18. The wavefront sensor module of claim 17 further comprising:
a compensating lens disposed substantially at the second window and having at least a portion configured to bend light to compensate removal of the objective lens when the illumination path is changed as a result of the removal of the objective lens.

* * * * *